US00PP21969P2

(12) United States Plant Patent
Hanes

(10) Patent No.: US PP21,969 P2
(45) Date of Patent: Jun. 7, 2011

(54) ***PETUNIA* PLANT NAMED 'PIC LITPINA'**

(50) Latin Name: *Petunia hybrida*
Varietal Denomination: Pic Litpina

(75) Inventor: Mitchell Hanes, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/804,407

(22) Filed: Jul. 21, 2010

(51) Int. Cl.
*A01H 5/00* (2006.01)

(52) U.S. Cl. ..... Plt./356

(58) Field of Classification Search ..... Plt./356
See application file for complete search history.

*Primary Examiner* — Kent L Bell
(74) *Attorney, Agent, or Firm* — S. Matthew Edwards

(57) ABSTRACT

A new *Petunia* plant named 'Pic Litpina' particularly distinguished by the small white and light red-purple colored flowers, good floriferousness with continuous flowering, early flowering, medium green foliage, initially semi-compact and then an outwardly spreading plant habit.

1 Drawing Sheet

Latin name of the genus and species of the plant claimed: *Petunia hybrida.*

Varietal denomination: 'Pic Litpina'.

BACKGROUND OF THE NEW PLANT

The present invention comprises a new *Petunia,* botanically known as *Petunia hybrida,* and hereinafter referred to by the variety name 'Pic Litpina'.

'Pic Litpina' is a product of a planned breeding program. The new cultivar has small white and light red-purple colored flowers, good floriferousness with continuous flowering, early flowering, medium green foliage, initially semi-compact and then an outwardly spreading plant habit.

'Pic Litpina' originated from a hybridization made in September 2001 in a controlled breeding environment in Gilroy, Calif. The female parent was the proprietary, unpatented plant designated '01-837-3', with white flowers and a less spreading habit.

The male parent of 'Pic Litpina' is a commercially available variety identified as 'Conbloss', U.S. Plant Pat. No. 13,556, with a more white flower color and larger foliage. The resultant seed was sown in March 2002.

'Pic Litpina' was selected as one flowering plant within the progeny of the stated cross in the June, 2002 in a controlled environment in Gilroy, Calif.

The first act of asexual reproduction of 'Pic Litpina' was accomplished when vegetative cuttings were propagated from the initial selection in June 2002 in a controlled environment in Gilroy, Calif.

BRIEF SUMMARY OF INVENTION

Horticultural examination of plants grown from cuttings of the plant initiated in June 2002, and continuing thereafter, has demonstrated that the combination of characteristics as herein disclosed for 'Pic Litpina' are firmly fixed and are retained through successive generations of asexual reproduction.

'Pic Litpina' has not been observed under all possible environmental conditions. The phenotype may vary significantly with variations in environment such as temperature, light intensity and day length.

A Plant Breeder's Right for this cultivar was applied for in Canada on Feb. 18, 2010 (#10-6850). 'Pic Litpina' has not been made publicly available more than one year prior to the filing of this application.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawing shows typical flower and foliage characteristics of 'Pic Litpina' with colors being as true as possible with an illustration of this type. The photographic drawing shows a flowering potted plant of the new variety growing in a 4 inch pot and a close-up of the flowers.

DETAILED BOTANICAL DESCRIPTION

The aforementioned photographs were taken in April 2010 from plants growing in a greenhouse trial in Gilroy, Calif. These plants were approximately 13-14 weeks of age. The plant descriptions and measurements were taken later on those very same plants in early June 2010 after growing outdoors a few weeks. They were about 16 weeks of age.

Color references are made to The Royal Horticultural Society Colour Chart (R.H.S.) 2001.

TABLE 1

DIFFERENCES BETWEEN THE NEW VARIETY 'PIC LITPINA' AND A SIMILAR VARIETY

| | 'Pic Litpina' | 'Conbloss' (U.S. Plant Pat. No. 13,556) |
|---|---|---|
| Flower color: | Light red-purple | White |
| Foliage length: | Shorter | Longer |

TABLE 1-continued

DIFFERENCES BETWEEN THE NEW VARIETY 'PIC LITPINA' AND A SIMILAR VARIETY

| | 'Pic Litpina' | 'Conbloss' (U.S. Plant Pat. No. 13,556) |
|---|---|---|
| Petiole length: | Shorter | Longer |
| Peduncle length: | Longer | Shorter |

Plant:

*Form, growth and habit.*—Initially semi-compact to outwardly spreading, strong and well branched habit, small foliage, and continuously flowering.

*Plant height.*—12 cm.

*Plant height* (*inflorescence included*).—14-16 cm.

*Plant width.*—40 cm.

*Garden performance and tolerance to weather.*—Very good.

*Crop time to flowering.*—About 8 -9 weeks.

Roots:

*Number of days to initiate roots and produce a rooted cutting.*—18-23 days at about 22 degrees C.

*Type.*—Fine, fibrous, free branching.

*Color.*—RHS N155B but whiter.

Foliage:

*Arrangement.*—Alternate, upper leaves sub-opposite.

*Immature, leaf color, upper surface.*—Between RHS 137A and RHS 137B.

*Lower surface.*—Closest to RHS 137C but a little lighter.

*Mature, leaf color, upper surface.*—Between RHS 137 A and RHS 137B.

*Lower surface.*—Closest to RHS 137C but a little lighter.

*Length.*—2.5-2.8 cm.

*Width.*—1.1 cm.

*Shape.*—Elliptical.

*Base shape.*—Attenuate.

*Apex shape.*—Acute.

*Margin.*—Entire.

*Texture, upper surface.*—Few glandular hairs along the margins.

*Lower surface.*—Few glandular hairs along the margins.

*Color of veins, upper surface.*—RHS 144C.

*Color of veins, lower surface.*—RHS 144C.

*Petiole color.*—RHS 144C.

*Length.*—0.3-0.4 cm.

*Diameter.*—0.2 cm.

*Texture.*—Few glandular hairs; pilose.

Stem:

*Color of stem.*—RHS 143A.

*Length of stem.*—18-20 cm.

*Diameter.*—0.3-0.4 cm.

*Length of internodes.*—0.3-0.5 cm.

*Texture.*—Glandular hairs; pilose.

*Color of peduncle.*—RHS 143A.

*Length of peduncle.*—2.5-2.7 cm.

*Peduncle diameter.*—0.15 cm.

*Texture.*—Glandular hairs; pilose.

Inflorescence:

*Type.*—Flowers appear solitary in upper leaf axis.

*Floret type.*—Funnel-shaped; 5 lobed petals; fused at the base; calyx, 5 deeply lobed sepals.

*Blooming habit.*—Continuous throughout the growing season. Good floriferousness.

*Quantity of inflorescences per plant.*—About 150.

*Lastingness of individual blooms on the plant.*—5-7 days.

*Fragrance.*—None.

Bud (just when showing color):

*Color.*—RHS N155C with RHS 1B but lighter basally.

*Length.*—3.0-3.5 cm.

*Width.*—0.5 cm.

*Shape.*—Oblong.

Immature inflorescence:

*Diameter.*—3.5-3.7 cm.

*Color, upper surface.*—Background of RHS N155B but white overlaid with blotches between RHS N74C and RHS N66D; and RHS N144A mid-veins.

*Lower surface.*—Closest to RHS N155B and RHS N144A mid-veins.

Mature inflorescence:

*Floret horizontal diameter.*—4.0 cm.

*Vertical depth.*—3.5 cm.

*Petal color, upper surface.*—Ground color of RHS N155B but whiter, heavily overlaid with blotches of closest to RHS N66D in varying hues that mature to lighter hues.

*Lower surface.*—RHS N155B but lighter with RHS N144A mid-veins, and a slight hue of the pink from the upper surface showing through.

*Petal apex shape.*—Retuse.

*Petal base shape.*—Fused.

*Petal margin.*—Entire.

*Waviness of petals.*—Moderate.

*Petal lobation.*—Moderate.

*Petal texture, upper surface.*—Papillose.

*Under surface.*—Papillose.

*Corolla tube color inside.*—RHS 155B overlaid slightly with RHS 155C but a little more yellow; with RHS N144A mid-veins.

*Outside.*—RHS 1C with RHS N144A mid-veins and RHS 144C veins.

*Corolla tube length.*—2.2-2.5 cm.

*Corolla texture, inside.*—Papillose.

*Outside.*—Glandular hairs; pilose.

Calyx:

*Color, upper surface.*—RHS 143A to RHS 143B.

*Lower surface.*—RHS 143A.

*Length.*—0.7 cm.

*Width.*—0.15 cm.

*Shape.*—Almost ligulate.

*Apex shape.*—Acute.

*Based.*—Fused.

*Margins.*—Entire.

*Texture, upper surface.*—Glandular hairs.

*Lower surface.*—Glandular hairs.

Reproductive organs:

*Pistil.*—1.

*Length.*—1.5-1.6 cm.

*Style color.*—RHS 145B.

*Style length.*—1.4 cm.

*Stigma color.*—RHS 145C with RHS 144B in the middle.

*Ovary color.*—RHS 143B.

*Stamens.*—5.

*Color of filaments.*—RHS 155B.

*Length filaments.*—1.5-1.7 cm.

*Anther color.*—RHS 155A.

*Anther length.*—0.2 cm.

*Anther shape.*—Elliptical to oval.

*Color of pollen.*—RHS 155B.

*Pollen amount.*—Moderate.

*Fertility/seed set.*—Has not been observed on this hybrid.

Disease/pest resistance: Disease/pest resistance has not been observed on this hybrid.

What is claimed is:

1. A new and distinct variety of *Petunia* plant named 'Pic Litpina' substantially as illustrated and described herein.

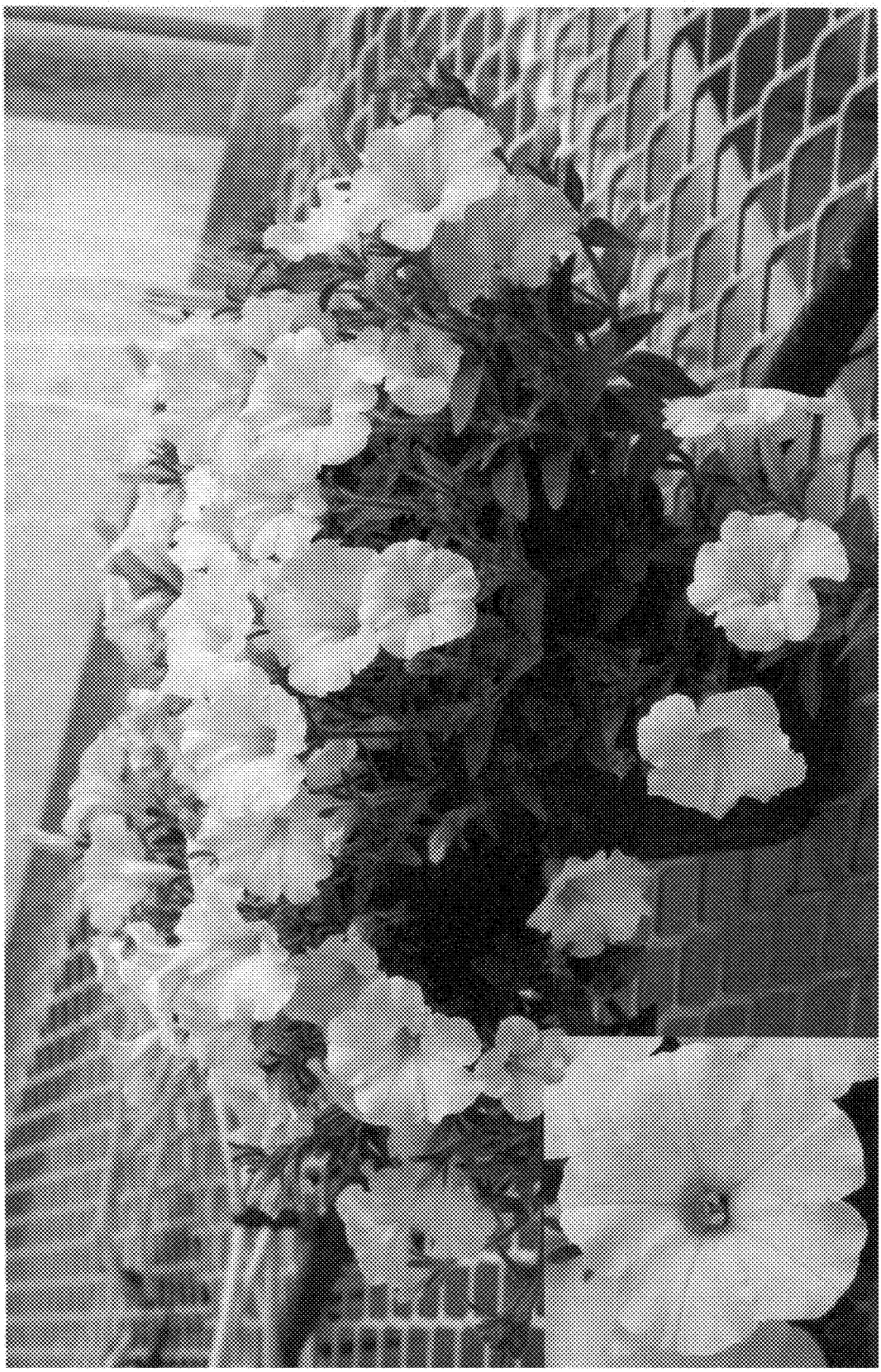

* * * * *